United States Patent
Fruetel et al.

(10) Patent No.: US 7,527,977 B1
(45) Date of Patent: *May 5, 2009

(54) PROTEIN DETECTION SYSTEM

(75) Inventors: Julie A. Fruetel, Livermore, CA (US); Gregory J. Fiechtner, Bethesda, MD (US); Dahv A. V. Kliner, San Ramon, CA (US); Andrew McIlroy, Livermore, CA (US)

(73) Assignee: Sandia Corporation, Livermore, CA (US)

( * ) Notice: Subject to any disclaimer, the term of this patent is extended or adjusted under 35 U.S.C. 154(b) by 834 days.

This patent is subject to a terminal disclaimer.

(21) Appl. No.: 11/087,942

(22) Filed: Mar. 22, 2005

Related U.S. Application Data

(60) Provisional application No. 60/555,591, filed on Mar. 22, 2004.

(51) Int. Cl.
*B01L 3/02* (2006.01)

(52) U.S. Cl. .............. 436/180; 422/82.11; 422/100

(58) Field of Classification Search .............. 422/99, 422/100, 102, 81, 82.11; 436/180, 174
See application file for complete search history.

(56) References Cited

U.S. PATENT DOCUMENTS

| | | | | |
|---|---|---|---|---|
| 5,528,040 A | | 6/1996 | Lehmann | 250/343 |
| 5,733,730 A | * | 3/1998 | De Lange | 435/6 |
| 5,986,768 A | * | 11/1999 | Pipino | 356/440 |
| 6,197,503 B1 | | 3/2001 | Vo-Dinh et al. | 435/6 |
| 6,270,641 B1 | * | 8/2001 | Griffiths et al. | 204/451 |
| 6,694,067 B1 | | 2/2004 | O'Keefe et al. | 385/12 |
| 6,765,656 B2 | | 7/2004 | Johnson | 356/73 |
| 6,839,140 B1 | | 1/2005 | O'Keefe et al. | 356/436 |
| 6,842,548 B2 | | 1/2005 | Loock et al. | 385/15 |
| 7,005,301 B2 | * | 2/2006 | Cummings et al. | 436/180 |

OTHER PUBLICATIONS

Hallock, A.J.; Berman, E.S.F.; Zare, R.N; "Direct Monitoring of Absorption in Solution by cavity Ring-Down Spectroscopy," *Analytical Chemistry*, v.74, pp. 1741-1743, Apr. 2002.

Xu, S.; Sha, G.; Xie, J.; "Cavity ring-down spectroscopy in the liquid phase," *Review of Scientific Instruments*, v.73(2), pp. 255-258, Feb. 2002.

Engein, R.; von Helden, G; van Roij, A.J.A.; Meijer, G.; "Cavity ring down spectroscopy on solid c60," *Journal of Chemical Physics*, v. 110(5), pp. 2732-2733, Feb. 1999.

Pipino, A.C.R.; Hudgens, J.W.; Huie, R.E.; "Evanescent wave cavity ring-down spectroscopy with a total-internal-reflection minicavity," *Review of Scientific Instrumentation*, v. 68(8), pp. 2978-2989, Aug. 1997.

Graham, C.R.; Leslie, D.; Squirrell, D.J.; "Gene probe assays on a fibre-optic evanescent wave biosensor," *Biosensors & Bioelectronics*, v.7, pp. 487-493, 1992.

* cited by examiner

*Primary Examiner*—Jill Warden
*Assistant Examiner*—Cedric Chan
(74) *Attorney, Agent, or Firm*—Timothy P. Evans

(57) ABSTRACT

The present embodiment describes a miniature, microfluidic, absorption-based sensor to detect proteins at sensitivities comparable to LIF but without the need for tagging. This instrument utilizes fiber-based evanescent-field cavity-ring-down spectroscopy, in combination with faceted prism microchannels. The combination of these techniques will increase the effective absorption path length by a factor of $10^3$ to $10^4$ (to ~1-$m$), thereby providing unprecedented sensitivity using direct absorption. The coupling of high-sensitivity absorption with high-performance microfluidic separation will enable real-time sensing of biological agents in aqueous samples (including aerosol collector fluids) and will provide a general method with spectral fingerprint capability for detecting specific bio-agents.

25 Claims, 4 Drawing Sheets

*FIG. 1C*   *FIG. 1D*

PROTEIN DETECTION SYSTEM

CROSS REFERENCE TO RELATED APPLICATIONS

This application claims priority to prior provisional U.S. Patent Application Ser. No. 60/555,591 originally filed Mar. 22, 2004 entitled "PATHOGEN DETECTION SYSTEM".

STATEMENT OF GOVERNMENT INTEREST

This invention was made with Government support under government contract no. DE-AC04-94AL85000 awarded by the U.S. Department of Energy to Sandia Corporation. The Government has certain rights in the invention, including a paid-up license and the right, in limited circumstances, to require the owner of any patent issuing in this invention to license others on reasonable terms.

BACKGROUND

Rapid detection of bio-agents is required in a number of applications, including monitoring water supplies, protecting critical facilities, process control, and hazard analysis by first responders. These applications also require high sensitivity and high specificity (i.e., low false-alarm rate), and they place substantial demands on the physical characteristics (size, weight, power consumption), reliability, and cost of the instrument. Sensors based on microfluidic separation and analysis of aqueous samples have the potential to simultaneously address all of these needs.

Instruments based on microfluidic separation of complex mixtures have emerged as nearly ideal platforms for identification of a wide range of biological compounds. In particular, it is of current interest to rapidly detect pathogenic biological compounds which could be used as weapons. However, such species are typically present in very low concentration and if rapid detection is of interest, e.g., detection in less than 1 minute (such as for detect-to-warn scenarios), time-consuming sample processing must be eliminated. Unfortunately, most current methods used to achieve a low detection limit rely on ultra-sensitive detection methods such as laser-induced fluorescence ("LIF") that require significant sample processing such as fluorescent tagging (e.g., U.S. Pat. No. 6,197,503, issued Mar. 6, 2001), to be effective. Other methods, therefore, are necessary.

In particular, the use of ring-down time of a light signal in a cavity (i.e., cavity ring-down spectroscopy or "CRDS") can be used to measure optical characteristics of an absorbing medium. Such optical cavities consist of two or more mirrors between which an optical signal is reflected to characterize the mirrors as well as the optical characteristics of an absorbing medium (e.g., gases, molecular beams, etc.) between the mirrors (see for instance U.S. Pat. No. 5,528,040, issued Jun. 18, 1996). This technique has also been used for evanescent wave spectroscopy (U.S. Pat. No. 5,835,231, issued Nov. 10, 1998).

However, while a number of high-sensitivity absorption methods have been developed for gas-phase applications, condensed-phase analogs have been slow to emerge, Until recently, applications in condensed phase have been limited generally to absorption measurements of films through evanescent field experiments on the surface of all-solid state cavities and to films deposited on windows inside the cavity (see Pipino et al., *Review of Scientific Instruments*, 1997, v. 68, pp. 2978-2989; and Engeln et al., *Journal of Chemical Physics*, 1999, v. 110, pp. 2732-2733).

Beginning in 2002, however, the application of CRDS to absorption measurements on liquid samples began to be reported (see Hallock et al., *Review of Scientific Instruments*, 2002, v. 74, pp. 1741-1743; and Xu et al., *Review of Scientific Instruments*, 2002, v. 73, pp. 255-258) and more recently a CRDS device has been shown interfaced with a microfluidic separation column through which light was passed and collected using optical fibers (U.S. Pat. No. 6,842,548, issued Jan. 11, 2005).

Unfortunately, application of absorption-based detection in microfluidic systems has been limited by poor sensitivity due to the short path lengths (e.g., 10 μm to 100 μm) characteristic of the channel width of most microfluidic devices.

To overcome this problem, a sensing system is described which comprises a light transmitting/sensing means utilizing a cavity-ringdown laser for generating an evanescent field in a short length of optical fiber, and a microfluidic separation channel having a series of connected, prism segments for rotating and broadening the path of a flowing liquid while minimizing the dispersion of that flow such as is described in co-pending, commonly-owned U.S. patent application Ser. No. 10/456,772 now U.S. Pat. No. 7,005,301, herein incorporated by reference. The combination of these techniques can increase the effective absorption path length in the microfluidic channel by a factor of $10^3$ or more, thereby providing the necessary sensitivity using direct absorption.

SUMMARY OF THE INVENTION

An embodiment of the present invention comprises coupling high-sensitivity absorption with high-performance microfluidic separation to enable real-time sensing of proteins and/or other biological compounds in liquid samples and to provide a general method having spectral "fingerprint" capability.

The present embodiment, therefore, will provide a novel approach to attain rapid, high sensitivity analysis in a reagent-less, microfluidic bioassay.

Finally, we note that these two techniques are highly complementary. For example, the evanescent field from the fiber extends into the liquid a distance on the order of the optical wavelength (~1 μm), which is less than the depth of typical microfluidic channel. Moreover, the wide, faceted microchannels can be made shallow (also ~1 μm in the present design), which is well matched to the fiber CRDS sensor. Similarly, the optical fiber eliminates beam divergence (diffraction), which degrades the sensitivity (signal strength) and the resolution in free-space approaches to long-path absorption.

BRIEF DESCRIPTION OF THE DRAWINGS

FIG. 1C shows a top-view simulation of a faceted prism microchannel having an extreme incidence angle (83°).

FIG. 1D shows the experimental performance of a proof-of-concept faceted prism microchannel with an extreme incidence angle (830) as viewed from above.

DETAILED DESCRIPTION OF THE EMBODIMENTS

The low detection limits required for bio-agent sensing necessitate the use of ultra-sensitive detection methods. The most commonly used technique is fluorescent tagging followed by ultraviolet ("UV") laser-induced fluorescence ("LIF"), which can detect protein concentrations as low as $10^{-12}$ M in microfluidic systems. Unfortunately, the time and reagents required for tagging preclude rapid detection or for long-term, unattended operation. In contrast, absorption-based methods offer the possibility of nearly universal detection without the need for labeling. Native protein detection is routinely performed in bench-top instruments using UV absorbance at 214 nm (for detecting the peptide molecule backbone) to 280 nm (for detecting protein side chains such as tryptophan). Moreover, certain specific proteins, such as myoglobin, contain chromophores that enable detection at visible wavelengths. In addition, near-infrared ("NIR") absorbance is used to detect proteins in complex matrices, such as food and in fermentation broth. By deconvolving the light spectra of these absorption-based methods, therefore, (e.g., using correlation spectroscopy) protein concentrations can be determined quantitatively.

Faceted Prism Microchannels:

Faceted prism microchannels are a new microfluidic design enabling rapid expansion and bending of microfluid flows without a corresponding increase in dispersion or distortion of an injected analyte sample band. The method, described in commonly owned U.S. patent application Ser. No. 10/456,772, teaches a microchannel comprising a series of connected channel segments each having a different permeability and orientation, with respect to its neighbor, on order to obtain a flow system which is piecewise uniform throughout the channel. Channel permeability is controlled by controlling the size and shape of the channel and because fluid channels of this type are typically rectangular in cross-section, the permeabilities of each segment are typically controlled by an abrupt change in channel depth at the interface adjoining adjacent segments. This geometry results in an interface disposed at an angle to the direction of flow into the interface between adjoining segments which causes the flow direction of the moving fluid to rotate as it crosses the interface. However, by carefully designing the geometries of low and high permeability regions in the channel, dispersion produced by the junctions is essentially eliminated.

Figure 1A:
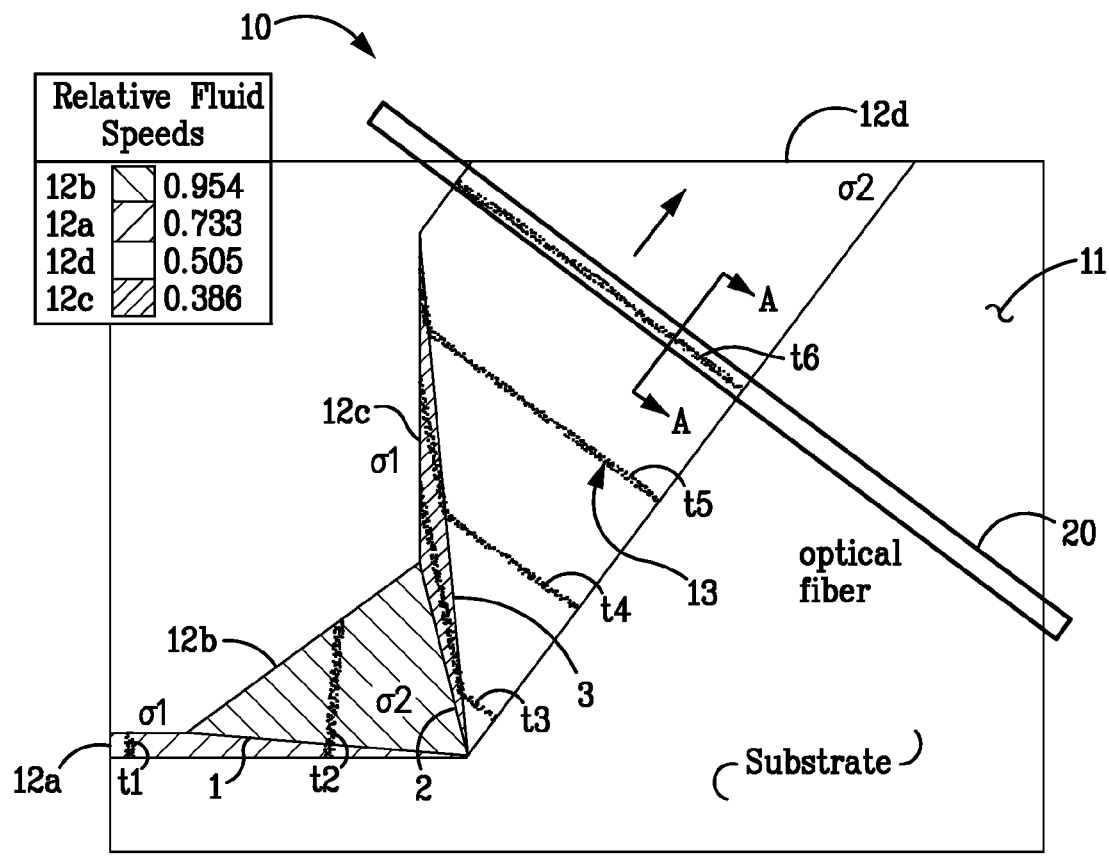
FIG. 1A shows a simulation of the proposed prototype protein detection system.
Figure 1B:
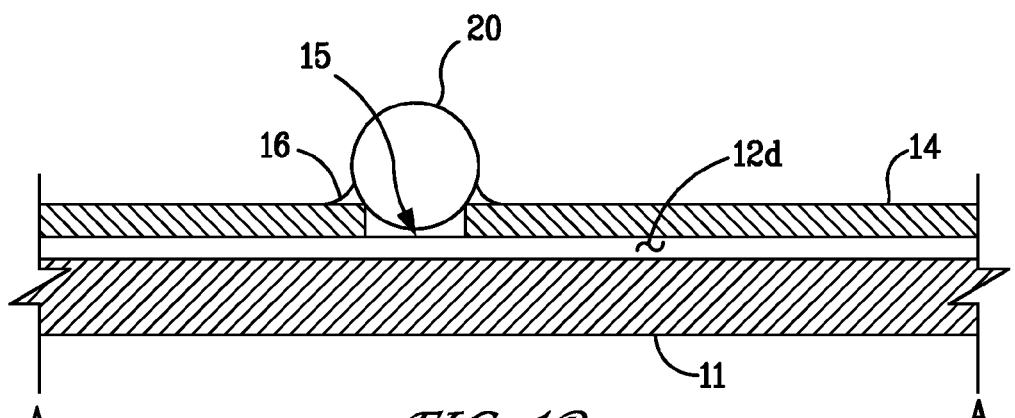
FIG. 1B shows a cross-section of the proposed prototype protein detection system through a portion of a channel segment and showing a polished section of optical fiber disposed in a slot etched in the detection system cover.

This capability is extremely useful for designing separation channels for capillary electrophoresis, where minimization of the diffusion time to the channel walls and retention of sample analyte band shape are important for high-speed, high-resolution separations. For example, FIGS. 1A and 1B show a prototype protein detection system 10 of just such a channel design that achieves a width expansion from 100 μm to about 1.44 mm as determined by numerical simulation. Therefore, by providing an optical probe across the expanded channel roughly parallel to an analyte sample band 13 this technique substantially increases the optical detection path length on-chip (i.e., the detection sensitivity) without loss of resolution for the analyte peaks. We recently fabricated the first faceted prism microchannels and demonstrated both redirection and expansion of microfluidic flows with minimal dispersion, as shown in FIG. 1C. Although the ultimate limit has not yet been determined, we anticipate increasing the channel width to at least 10-mm, which would yield a $10^2$ to $10^3$ fold improvement in sensitivity.

FIG. 1A provides, therefore, an illustration of the prototype protein detection system 10 comprising a plurality of connected microchannel segments 12a-12d having different cross-sectional areas etched into a substrate 11, an optical fiber 20 for transmitting an excitation signal and receiving an absorption response, and a cover 14 transparent to a wide range of electromagnetic radiation, to both close the top of the protein detection system and to provide a surface on which to mount the optical fiber. Not shown are the electrical paraphernalia used to drive electrokinetic flow through the channel and the laser and laser optics necessary to pump the CRDS cavity. Materials suitable for preparing the microchannel system include glass, quartz, or silicon.

Disposed over the faceted microchannel segments is transparent cover 14 to both close the microchannel and to provide a surface for mounting optical fiber 20. Analyte band 13 is shown injected at time t1 into channel facet 12a and at various positions at times t2-t6 respectively as it progresses through faceted microchannel segments 12b-d. The position of detector optical fiber 20, although not critical, is located so as to be about parallel to analyte band 13 at a time about equivalent to time t6.

Key to the design of the detection system is the design of the various connected segments 12a-12d of the faceted microchannel prepared as taught by U.S. patent application Ser. No. 10/456,772. In the present example, each of the channel segments 12a, 12b, 12c, and 12d, has a generally rectangular cross-section and a particular permeability, σ, defined by its cross-sectional area and alternately deep, designated as σ1, and shallow, designated as σ2, (the present example permeabilities σ1 and σ2 are represented by channel depths of about 10 μm and 1.μm, respectively). Moreover, adjoining channel segments are oriented with respect to each other such that fluid flowing from one segment to the next is constrained by a compatibility condition, $$\frac{\tan\theta_1}{\sigma_1} = \frac{\tan\theta_2}{\sigma_2}, \tag{1}$$

wherein the angle, θ, in each adjoining segment, is measured between a vector normal to the interface between the segments, and the vector flow of the fluid entering ($\theta_1$), and leaving ($\theta_2$), the interface between the two segments. This condition also gives rise to several other relationships, including:

$$u_1 \sin\theta_1 = u_2 \sin\theta_2, \tag{2}$$

and $$\frac{w_1}{\cos\theta_1} = \frac{w_2}{\cos\theta_2}, \tag{3}$$

where u is the relative speed of the fluid flow through the particular channel segment, and w, is the cross-sectional width of that segment.

Now, the simulation shown in FIG. 1A, describes the relative, or normalized, flow speed, U, in each of the four segments and is shown numerically in the upper left corner of the figure. The choice of channel orientation angles is arbitrary but constrained by Eq. 1 and by a limitation on the maximum angle through which the fluid may be turned while still maintaining piece-wise uniformity of flow. Moreover, to eliminate skew in each prismatic channel section, there is a constraining relation between inlet and outlet flow angles for each faceted interface. As shown in commonly-owned U.S. patent application Ser. No. 10/456,772 this "critical" angle is equal to $$\theta_c = (\theta_1 - \theta_2)_{Max} = 2\tan^{-1}\left(\sqrt{\frac{\sigma_1}{\sigma_2}}\right) - \frac{\pi}{2}. \quad (4)$$

For example, if the ratio of the channel permeability is about 10:1 the maximum permitted turning angle is therefore about 54.9°. By designing a flow channel in this way it is possible to expand the width of the initial incoming flow many times without destroying the integrity and continuity of a analyte sample "band" injected into the incoming flow as it passes through the various segments of the flow channel.

In particular, simulated flow system 10 is characterized by channel interfaces 1, 2, and 3, between segments 12a and 12b, 12b and 12c, and 12c and 12d, respectively. The large interfaces in the first and third channel segments serve to expand the width of the fluid to flow. Construction of the channel system is preformed as taught by commonly-owned U.S. patent application Ser. No. 10/456,772. By using Eqs. (1) and (3), and selecting an initial channel width of 0.1 mm and incoming fluid incident to channel interfaces 1, 2, and 3 at angles of 85°, 23°, and 85°, respectively it can be shown that the flow simulated in FIG. 1A can be expanded by a factor of greater than 14 as seen in TABLE 1 below. Notice that the values of relative speed, $u_i$, calculated using Eq. 2, agree well with those shown in FIG. 1A, assuming an initial entering relative speed of 0.73.

Finally, in an effort to experimentally confirm the basis for the simulation FIG. 1A a simple faceted prism microchannel having an extreme fluid incidence angle of 83° was prepared and tested. The experimental results of this test are shown in FIG. 1D in which fluorescent particles were imaged as they traversed the channel producing visible streaks (simulated streak line 50 has been superimposed on the image) showing that streaklines are straight and parallel to the side walls in each section. The channel depths used for the experimental verification were 10 μm and 1.0 μm. The width of the microchannels was 150 μm. A simulation of the same channel system is shown in FIG. 1C.

TABLE 1

|  | 1 | | 2 | | 3 | |
| --- | --- | --- | --- | --- | --- | --- |
|  | 12a | 12b | 12b | 12c | 12c | 12d |
| $\theta_i$ | 85° | 49° | 23° | 76° | 85° | 49° |
| $w_i$ | 100μ | 740μ | 740μ | 190μ | 190μ | 1430μ |
| $\sigma_i$ | 10μ | 1μ | 1μ | 10μ | 10μ | 1μ |
| $u_i$ | 0.73 | 0.97 | 0.97 | 0.39 | 0.39 | 0.51 |

Fiber-Based Evanescent-Field Cavity-Ringdown Absorption Spectroscopy:

Cavity-ringdown spectroscopy ("CRDS") is an ultra-sensitive absorption technique that has been widely applied in combustion research and other gas-phase applications requiring low detection limits for trace species. In this method, (taught, for instance, by U.S. Pat. Nos. 6,842,548 and 5,528,040, both herein incorporated by reference) the sample is contained within an optical cavity formed by two or more high-reflectivity mirrors, and the output of a pulsed laser is launched into the cavity. In a high-finesse cavity, the pulse can make hundreds or even thousands of round-trips, thereby increasing the effective absorption path length. When the laser is tuned to a wavelength that is absorbed by an analyte, its concentration is determined by a change in either the cavity decay time or in the signal intensity measured by monitoring the optical leakage through one of the cavity mirrors, typically with a device such as a photomultiplier tube or a CCD array. CRDS has comparable sensitivity to LIF, and it has all of the usual advantages associated with absorption spectroscopy: nearly universal detection capability (including non-fluorescent molecules), absolute calibration (for quantitative measurements), and applicability over a broad wavelength region (e.g., electronic transitions, vibrational transitions, overtones). More recently, variants of CRDS have emerged that use continuous wave ("CW") lasers (e.g., integrated cavity output spectroscopy). However, CRDS has never been used in microfluidic systems for on-chip detection because current methods for coupling light into such devices are incompatible with the requirement of a high-finesse cavity.

Figure 2A:
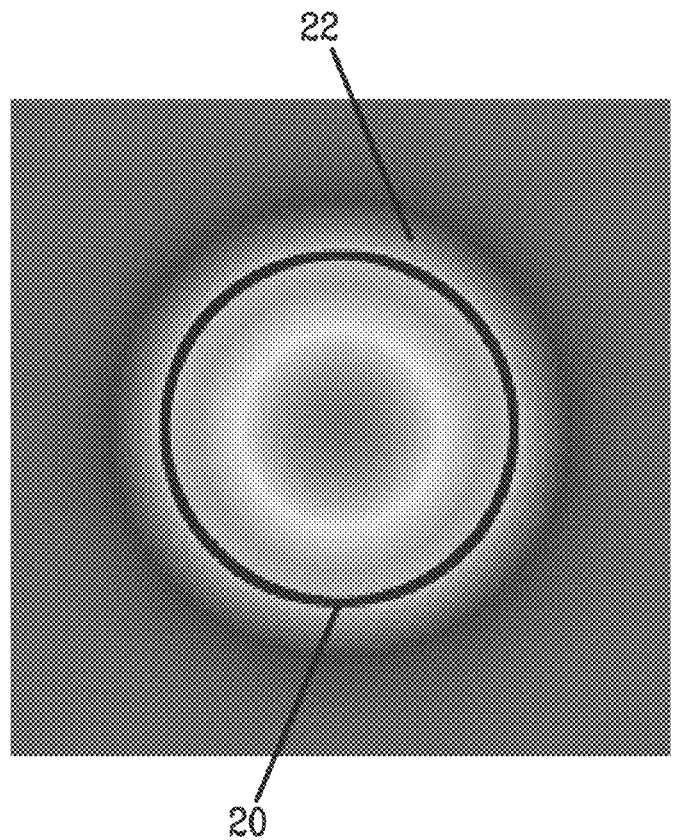
FIG. 2A illustrates the evanescent field 22 formed around an optical fiber 20 carrying a laser light wave.
Figure 2B:
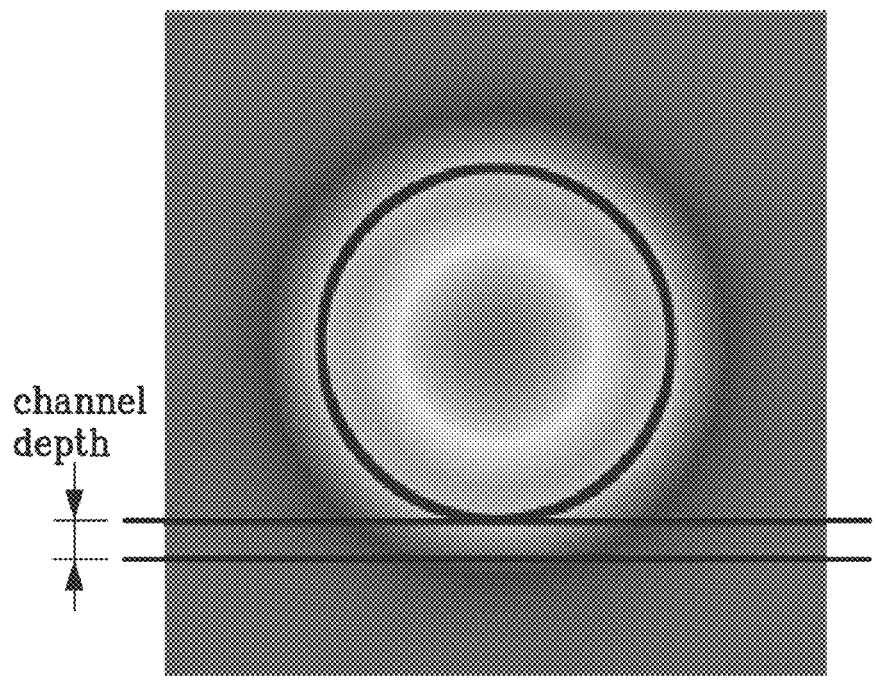
FIG. 2B illustrates the extant evanescent field is comparable to the depth of the faceted prism microchannel used in the present embodiments of a detection system.

We address the coupling problem by constructing a CRDS cavity using a low-loss, single-mode optical fiber similar to those used for telecommunications. In a single-mode fiber, the electric field of the light extends into a region 22 outside of the core of fiber 20 as shown in FIG. 2A. By polishing away the cladding or tapering the fiber, this evanescent field can be exposed and allowed to interact with the surrounding environment. Further, in the on-chip protein detection system 10 shown in FIG. 1A, the evanescent field would be brought in contact with (shallow) expanded microchannel facet 12d, shown in FIG. 1A, either by laying the polished fiber directly onto the surface of assembly 10 (and therefore onto cover 14), or, as shown in FIG. 1B, by introducing a slot 15 into cover 14, laying a section of optical fiber 20 into this slot, and securing the fiber in place with a sealing agent 16 such as an adhesive. If used, slot 15 can either penetrate part-way or completely through the thickness of the cover. However, since it is important not to interfere with fluid flow, if slot 15 passes through cover 14 the width of the slot will be dependent upon the thickness of cover 14 but at least less than the of average diameter of optical fiber 20.

Absorption by the analyte band then will be detected by measuring the change in either the cavity decay time or signal intensity when the analyte band 13 passes by fiber 20 and through field 22.

As with gas-phase CRDS, detection sensitivity is increased due to a multiplicity of round-trip passes made by each light pulse entering the cavity. The effective path length of the pulse is, therefore, increased by an anticipated factor of 50 to 100 in comparison to a single-pass measurement.

Figure 3:
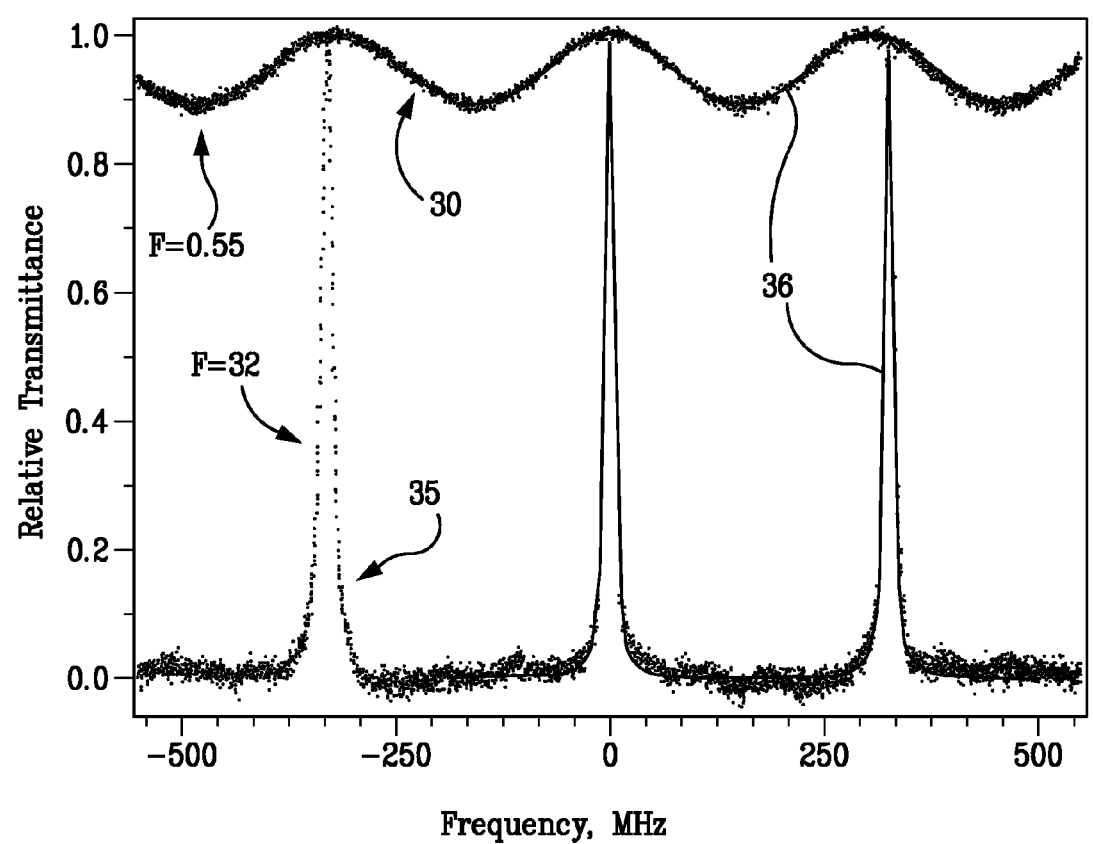
FIG. 3 shows the transmittance through 28-cm single-mode optical fibers (fiber cavities) as a function of wavelength, wherein the upper curve shows measurements for an uncoated fiber in which the cavity was formed by fiber end faces and the lower curve shows data recorded following gold coating the fiber faces.

We have recently fabricated optical cavities by gold-coating the end faces of single-mode fibers. Using coatings with ~80% reflectivity, we attained a finesse, of 10 (corresponding to 10 passes through the sample in 3 e-folding times of the cavity); the finesse was limited by the reflectivity of the gold coatings which we were able to provide in-house. The effect of coating the ends of the optical fiber cavity is shown in FIG. 3 wherein the transmittance as a function of wavelength is measured through a 28-cm length of single-mode optical fiber. Upper curve 30 shows signal measurements for an uncoated fiber in which the cavity was formed by the 3.5% reflectivity of the "native" fiber end faces. Lower curve 35 shows the signal measurements taken from the same fiber following gold coating of the fiber faces. Lines 36 are regression "fits" from which the finesses (shown in FIG. 3 as "F") were determined. The measurements were performed using a narrow-linewidth 1550 nm laser, which was scanned over a spectral region of 1500 MHz (0.012 nm).

Figure 4:
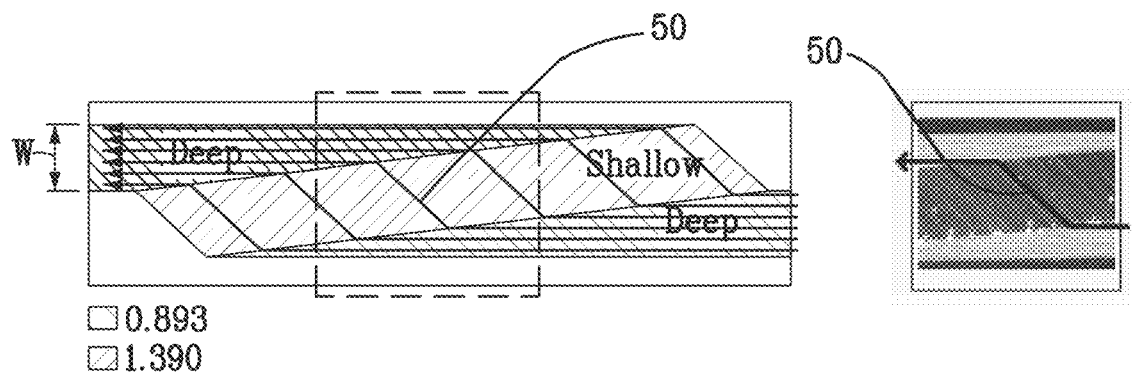
FIG. 4 illustrates the manner in which one or more laser light sources are directed at the interior of an optical fiber for the purpose of blazing a Bragg diffraction grating in the optical fiber.
Figure 4:
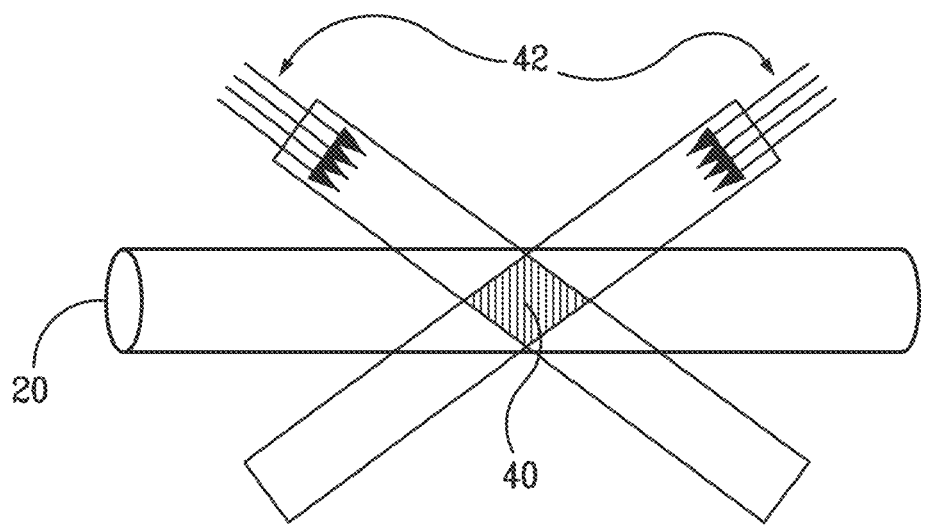

In later embodiments, dichroic coatings and Bragg gratings 40 which are known to be more durable and which have reflectivities >99% will be written into the fiber, as shown in FIG. 4, using one or more laser light sources 32 are directed at the interior of optical fiber 20. Bragg gratings 40 are placed at two locations to define the desired optical cavity. Lastly, separate embodiments will use more than one optical fiber.

A NIR laser operating at a wavelength of about 1500 nm, where proteins exhibit a distinct absorption feature corresponding to the amide stretch overtone is believed to be the best mode. Because proteins contain at least as many amide bonds as amino acid residues (e.g., botulinum toxin contains about 1300 such amino acid residues), detection at this wavelength should be more sensitive to proteins than to other small molecules and impurities (including soot). Improved specificity will be possible by probing at multiple wavelengths to generate a protein spectral fingerprint. In addition, the design of the microfluidic absorbance cell is general and can be used with other laser sources and detection schemes. Furthermore, test detection based upon UV absorbance and on refractive-index modulation, although as yet untested, is considered to be a further embodiment of the invention.

Those skilled in the art will recognize, or be able to ascertain using routine experimentation, variations of the embodiments and examples described herein. Such variations are intended to be within the scope of the invention and are covered by the appended claims.

What is claimed is:

1. A protein detection system, comprising:

a microfluidic channel disposed on a substrate body, said microfluidic channel comprising a plurality of connected channel regions, wherein each of said channel regions comprises a uniform rectangular cross-section, a longitudinal axis, and first and second side walls each aligned substantially parallel to said longitudinal axis, wherein at least first and second channel regions intersect at a first intersection plane passing through an intersection between said respective first side walls and said respective second side walls of said at least first and second channel regions, wherein a normal to said first intersection plane is oriented at a first angle, $\theta_{11}$, with respect to said longitudinal axis of said first channel region, and oriented at a second angle, $\theta_{12}$, with respect to the longitudinal axis of said second channel region; and means for establishing a first average permeability, $\overline{\sigma}_1$, in said first channel region, wherein $0.75\sigma_1<\overline{\sigma}_1<1.25\sigma_1$ and means for establishing a second average permeability, $\overline{\sigma}_2$, in said second channel region, wherein $0.75\sigma_2<\overline{\sigma}_2<1.25\sigma_2$, wherein $\sigma_1$ and $\sigma_2$ are first and second predetermined design permeabilities related by a compatibility condition comprising $$\frac{\tan\theta_{11}}{\sigma_1}=\frac{\tan\theta_{12}}{\sigma_2},$$

wherein a fluid flowing from said first channel region into said second channel region and comprising a flux that is substantially uniform in said first channel region, remains substantially uniform in said second channel region;

an electrical power supply and electrodes disposed at first and second ends of said microfluidic channel;

a cover transparent to at least some wavelengths of electromagnetic radiation covering said microfluidic channel;

a single mode optical fiber comprising a core and a cladding disposed on said cover, said optical fiber further comprising an optical cavity spanning said microfluidic channel, said optical cavity comprising partially transmissive means disposed on either side of said microfluidic channel, said optical fiber is tapered or thinned to remove some or all of said cladding along a length of said optical cavity;

a laser source optically coupled into said optical fiber; and means for measuring the decay time of said optical cavity.

2. The system of claim 1, wherein $\sigma_1>\sigma_2$.

3. The system of claim 2, wherein said means for establishing first and second predetermined permeabilities comprises providing channel regions having different depths.

4. The system of claim 3, wherein said depth of said first channel region is between about 2 times and 1000 times greater than the depth of said second channel region.

5. The system of claim 1, wherein said partially transmissive means comprises a mirror disposed at each end of said optical cavity, wherein at least one of said mirrors comprises an aperture.

6. The system of claim 5, wherein the mirrors are formed by polishing opposite ends of said optical fiber and subsequently coating said polished end with a layer of gold.

7. The system of claim 1, wherein partially transmissive means comprise a Bragg grating disposed in said optical fiber.

8. The system of claim 1, wherein said optical cavity is tapered or thinned by removing a portion of said optical fiber exterior surface along a line parallel to a longitudinal axis of said optical fiber.

9. The system of claim 1, wherein said cover comprises a slot etched into a top surface of said cover.

10. The system of claim 9, wherein the slot is etched through a thickness of said cover.

11. The system of claim 9, wherein the slot is etched part way through a thickness of said cover.

12. The system of claim 10, wherein said slot comprising a length and width sufficient to contain said optical cavity while maintaining the optical cavity at or above a bottom surface of said cover.

13. The system of claim 2, wherein said first electrode is held at a potential more negative than said second electrode.

14. The system of claim 2, wherein said first electrode is held at a potential more positive than said second electrode.

15. The system of claim 2, further comprising:

a third channel region intersects said second channel regions at a second intersection plane passing through an intersection between said respective first side walls and said respective second side walls of said second and third channel regions, and wherein a normal to said second intersection plane is oriented at an angle, $\theta_{21}$, with respect to said longitudinal axis of said second channel region, and oriented at an angle, $\theta_{22}$, with respect to the longitudinal axis of said third channel region; and means for establishing a third channel permeability, $\overline{\sigma}_3$, in said third channel region, wherein $0.75\sigma_3<\overline{\sigma}_3<1.25\sigma_3$, where $\sigma_3$, is a third predetermined design permeability related to said second predetermined design permeability by a compatibility condition comprising $$\frac{\tan\theta_{21}}{\sigma_2} = \frac{\tan\theta_{22}}{\sigma_3},$$

wherein a fluid flowing from said second channel region into said third channel region and comprising a flux that is substantially-uniform in said second channel region remains substantially uniform in said third channel region.

16. The system of claim 15, wherein $\sigma_1 \cong \sigma_3$.

17. The system of claim 15, wherein said means for establishing said first, second and third predetermined permeabilities comprises providing channel regions having different depths.

18. The system of claim 15, wherein said partially transmissive means comprises a mirror disposed at each end of said optical cavity, wherein at least one of said mirrors comprises an aperture.

19. The system of claim 18, wherein the mirrors are formed by polishing opposite ends of said optical fiber and subsequently coating said polished end with a layer of gold.

20. The system of claim 15, wherein partially transmissive means comprise a Bragg grating disposed in said optical fiber.

21. The system of claim 15, wherein said optical cavity is tapered or thinned by removing a portion of said optical fiber exterior surface along a line parallel to a longitudinal axis of said optical fiber.

22. The system of claim 15, wherein said cover comprises a slot etched into a top surface of said cover.

23. The system of claim 22, wherein the slot is etched through a thickness of said cover.

24. The system of claim 22, wherein the slot is etched part way through a thickness of said cover.

25. The system of claim 22, wherein said slot comprising a length and width sufficient to contain said optical cavity while maintaining the optical cavity at or above a bottom surface of said cover.

* * * * *